(12) United States Patent
Lorenzo

(10) Patent No.: US 7,192,409 B2
(45) Date of Patent: Mar. 20, 2007

(54) COMFORT BANDAGE

(76) Inventor: Aida Iris Lorenzo, 19 Broadway, Valley Stream, NY (US) 11580

(*) Notice: Subject to any disclaimer, the term of this patent is extended or adjusted under 35 U.S.C. 154(b) by 0 days.

(21) Appl. No.: 10/744,902

(22) Filed: Dec. 22, 2003

(65) Prior Publication Data

US 2005/0004501 A1    Jan. 6, 2005

(51) Int. Cl.
*A61F 5/00* (2006.01)
*A41C 3/00* (2006.01)

(52) U.S. Cl. .............. 602/19; 450/57; 2/67; 2/92

(58) Field of Classification Search ............. 606/204; 602/75, 79, 19, 60, 61, 63; 2/312, 92, 267; 450/1, 4, 57, 63
See application file for complete search history.

(56) References Cited

U.S. PATENT DOCUMENTS

| | | |
|---|---|---|
| 1,592,496 A | 7/1926 | Madden |
| 3,189,028 A | 6/1965 | Dormire |
| 3,968,803 A | 7/1976 | Hyman |
| 4,022,197 A | 5/1977 | Castiglia |
| 4,187,855 A | 2/1980 | Paulus et al. |
| 5,005,567 A | 4/1991 | Gilman et al. |
| 5,098,331 A | 3/1992 | Corrado |
| 5,152,741 A | 10/1992 | Farnio |
| 5,158,541 A | 10/1992 | McCurley |
| 5,277,700 A | 1/1994 | Smith |
| 5,429,593 A | 7/1995 | Matory |
| 5,527,270 A | 6/1996 | Chase et al. |
| 5,807,160 A | 9/1998 | Wehmeyer |
| 5,843,018 A | 12/1998 | Shesol et al. |
| 6,439,958 B1 * | 8/2002 | Lorenzo ............. 450/1 |
| 6,512,159 B1 | 1/2003 | Shesol et al. |
| 6,887,123 B2 * | 5/2005 | Lorenzo ............. 450/57 |

* cited by examiner

*Primary Examiner*—Kim M. Lewis
(74) *Attorney, Agent, or Firm*—Ward & Olivo (57) ABSTRACT

A band for use for breast stabilization from lateral gravitational shifting is disclosed. The band comprises a strip to encircle the body, a first section comprising a semi-cylindrical component of a sponge-like material at one end and a nap material patch on its outer surface with a cylindrical side placed over the sternum, and a second section fro connecting an end of the body strip to encircle a user's body. The band comprises at least one fenestration to enable breast exposure.

1 Claim, 11 Drawing Sheets

COMFORT BANDAGE

BACKGROUND OF THE INVENTION

This invention is directed to a bandage for wound dressing, which may be an underclothes garment, and more particularly to a garment used in the medical field to ease and prevent lateral gravitational breast shifting while the user is in the side-lying position.

In the past a traditional brassiere has been used to support the breast while in the upright position but does not provide adequate lateral support for the side-lying position. The brassiere usually has metal or plastic parts which when used while sleeping or extended periods of bed rest produces pressure points and skin irritation.

Previous prior art has addressed the issue of bodily support through the use of undergarments. For example, U.S. Pat. No. 1,592,496 to Madden discloses a shirt with padding on the inner layer to relieve bodily soreness while in the reclining position. Also, Castiglia, U.S. Pat. No. 4,022,197, teaches the use of a band to support the rib cage, but does not address its use in the laying position. Neither Castiglia nor Madden, however, discuss the importance of supporting the breasts in the side-lying position.

Furthermore, prior art has addressed various ways to support breasts, especially for medical purposes. U.S. Pat. No. 3,189,028 to Dormire discloses the use of a breast support for enlarged breasts during and following pregnancy. The band, however, does not address comfort in the side-lying position or provide padding for the absorption of perspiration.

U.S. Pat. No. 3,968,803 to Hyman provides for a surgical chest dressing comprising an encircling band with shoulder straps. The dressing disclosed is an attempt to improve on previous methods for bandaging after a mastectomy operation. However, no padding is included to aid in support of the breasts. If absorbent dressing is required, cloth and tape are applied and then the chest dressing according to the invention is put on the patient. The use of adhesive tape may further irritate the skin, thereby further irritating the patient following chest surgery.

U.S. Pat. No. 4,187,855 to Paulus et al. discloses a brassiere-type garment for wearing following breast surgery. The elongated bodice assists in holding the garment in place. The device includes padding which forms breast substitutes following a mastectomy. The padding does not serve to support the breasts in a side-lying position.

U.S. Pat. No. 5,098,331, issued to Corrado, provides for a surgical chest dressing following surgery for breast augmentation. The disclosure does not provide for any type of padding for support, but merely provides for an elastic band to prevent movement through application of pressure. The pressure, however, may make the wearer uncomfortable.

U.S. Pat. No. 5,152,741 to Farnio and U.S. Pat. No. 5,538,502 to Johnstone both disclose a surgical chest dressing that provide support structures for the sides of the chest. Neither provide for the cushioned padding to aid in support of the breasts in the side-lying position or for the absorption of fluids.

U.S. Pat. No. 5,158,541 to McCurley teaches a mastectomy compression surgical brassiere with shoulder straps, lined brassiere cups, and a rectangular compression pad. The pad serves as a surgical dressing pad and the brassiere holds it firmly in place. However, the invention provides no padding for the remaining breast to support it in the side-lying position and no inframammary support would be required after a mastectomy.

U.S. Pat. No. 5,429,593 to Matory and U.S. Pat. No. 5,527,270 to Chase et al. both provide for dressings following chest surgery. Neither, however, account for the support of the breasts, nor provide padding.

Shesol et al., in U.S. Pat. No. 5,843,018, teaches a emollient carrier device for delivering an application of an emollient. The emollient is placed on a padding which may be applied to the chest, the padding does not provide for breast support.

In addition to bandages for breasts, various bandages have been developed for the face and other body parts. U.S. Pat. No. 5,005,567 to Gilman et al. ("Gilman") discloses a method for treating leg wounds. The method involves applying a dressing to a leg wound and then putting an elastic stocking over the dressing. The method described by Gilman, however, does not attach the dressing to the stocking, which could result in undesirable slippage of the dressing from the wound. In addition, Gilman's method results in compression to a much larger surface area than necessary, resulting in additional discomfort.

Smith disclosed a facial bandage in U.S. Pat. No. 5,277,700. Her bandage is an adjustable facial dressing for compression or for support of facial features for medical treatment. However, the facial bandage disclosed does not provide padding or absorbent material to soak up drainage from wounds.

Shesol et al., in U.S. Pat. No. 6,512,159, also disclose a facial bandage, specifically, a facial wound dressing support device. The device is typically worn as a mask on the face as a support device following facial injury or surgery, and is formed of a stretchable woven material. While the device may absorb wound drainage, the fluids would diffuse to areas of the face where there is no wound. In these cases, it is necessary to replace the whole bandage, thereby upsetting a recovering patient, rather than merely replace a piece of padding.

It is apparent that the need exists for an improved device for the support of the breasts in the lateral position, as well as for wound dressings in general. The present invention is not worn as a "traditional" undergarment and does not serve the same function of strapped breast support while standing in an upright position.

BRIEF SUMMARY OF THE INVENTION

The object of the present invention is to provide a comfort band which is constructed from a combination of soft stretch woven materials with a semi-cylindrical shaped bolster centrally placed over the sternum which may be either c-shaped or sickle-shaped to accommodate either right or left breast bolstering or incision fitting. The remaining band is then wrapped under the arms and around the chest with a band and preferably secured with a VELCRO™ (or similar hook and loop fastener) fastener thereby preventing lateral breast shifting when the patient is in the side-laying position. The stretchable and adaptable band or garment of the invention consists of a relatively wide body strip which accommodates breast coverage, or achieves exposure with a fenestrated band.

This invention is directed to the medical field as well as women's personal care. A more specific object of this invention is to provide a breast comfort band that will ease the discomfort of lateral breast shifting which occurs in the side lying position and caused by breast engorgement such as in mastitis, postpartum engorgement, breast implants and anatomically heavy and large size of breast. When used post augmentation the band with chosen shape will support new implants, maintain contour of newly shaped breasts and retard fluid formation or bloody fluid to prevent the formation of a hematoma or seroma. In addition, it will absorb perspiration and prevent skin breakdown/deterioration caused by perspiration and prolonged direct skin contact such as seen in hospitalized geriatric patients. Immobile geriatric patients who favor the side-lying position and have flaccid breasts experience skin deterioration of the breast due to one breast resting on the other. This would be prevented with the breast saver comfort band in place, minimizing tissue injury/deterioration as well as reducing the incidence of nosocomial infections due to open skin ulcerations. This preventative practice will reduce medical care required such as use of antibiotic ointments or medicated gauzes to prevent any open skin from receiving pathogenic bacteria. The band may also be used to absorb serous or sanguineous drainage when used post-operatively with breast procedures such as in medial breast lumpectomy. The band's thickness measures only 2–4 mm's, it is not bulky and has no metal or plastic parts, thereby reducing the risk of creating new pressure points on fragile skin or dependent area. Unlike traditional brassieres the comfort band is used at night for lateral breast support.

In women's personal care the band will absorb uncomfortable perspiration from in between the breast while in the side lying position as well as reduce or prevent medial breast wrinkling in mature women caused by extended periods of lateral breast shifting, especially those with sun skin damage. This wrinkling preventative measure may be used in conjunction with topical cosmetic creams or lotions.

Other objects, features, and characteristics of the present invention, as well as the methods of operation and functions of the related elements of the structure, and the combination of parts and economies of manufacture, will become more apparent upon consideration of the following detailed description with reference to the accompanying drawings, all of which form a part of this specification.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which.

DETAILED DESCRIPTION OF THE INVENTION

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention. The following presents a detailed description of a preferred embodiment (as well as some alternative embodiments) of the present invention.

A length of stretchable woven material capable of longitudinal and transverse stretching is set flat wherein its right-sided longest half has a suitable fastening means, i.e. a nap pile patch, secured. A corresponding hook strip component is secured on the left adjacent half. A semi-cylindrical sponge-like material, or pillow, with its flat surface up to the back of the nap pile fastening means is placed between the material and is enclosed by seams at its right and left side with permanent seams to the bottom length and the left side of the band. The band is then donned by placing the cylindrical surface over the sternum, extending and stretching the band to accommodate the circumference of the chest and achieve breast coverage and in an overlapping relationship secured with its fastener in the front of the chest onto the flat surface of the semi-cylindrical component. The band is of one piece construction which is easily applied to the patient while in bed from either right or left orientation.

Figure 1:
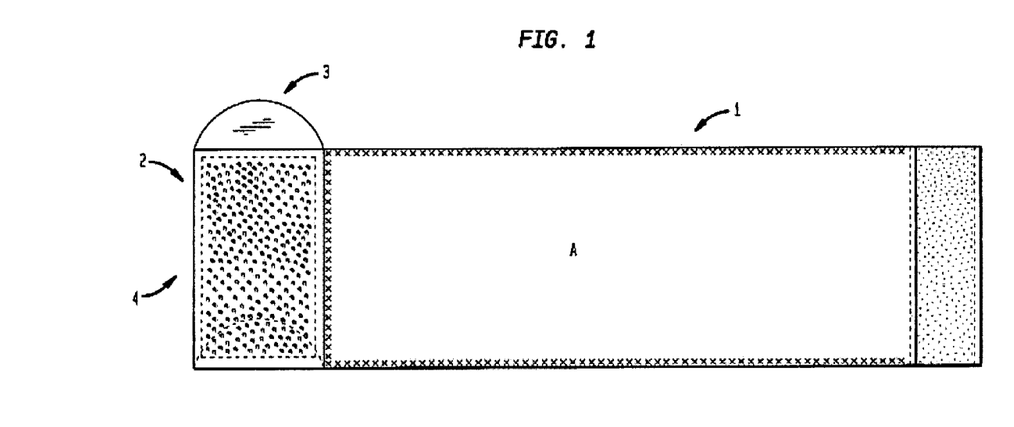
FIG. 1 is a perspective view of the solid band of the comfort band before it is applied to the patient.
Figure 2:
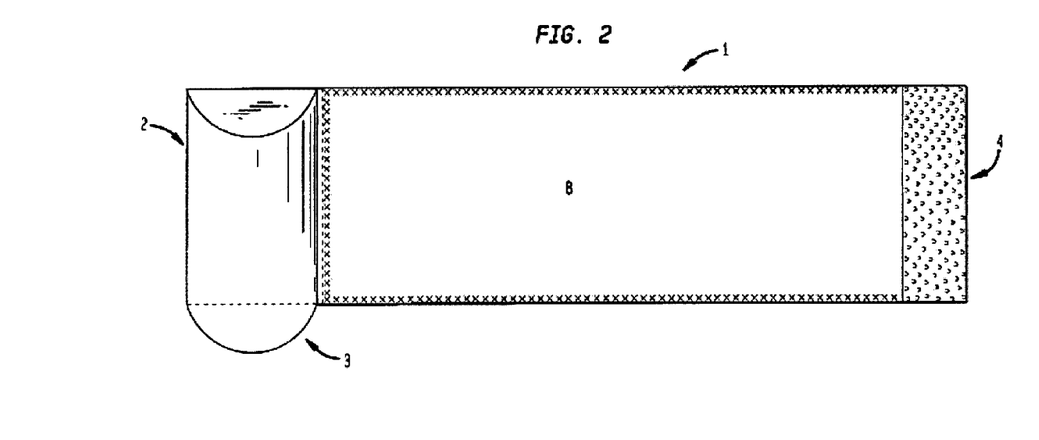
FIG. 2 is a perspective view of the solid band as it would be applied to the patient and the body engaging surface.

The stretchable and adaptable band or garment of the invention consists of a relatively wide solid body band 1, depicted in FIGS. 1 and 2, which encircles the chest and accommodates breast coverage. Breast exposure is achieved with a Fenestrated band 1, shown in FIGS. 3 and 4. The band end is connected to a space-occupying semi-cylindrical sponge-like material 2, shown in FIGS. 1, 2, 3, and 4, which serves as a bolster for the breast.

In use, the cylindrical shaped surface at one end 3, represented in FIGS. 1, 2, 3, and 4, is centrally placed over the sternum, the connecting band 1, is then wrapped under the arms and around the chest and preferably secured in the front in an overlapping relationship with a VELCRO™ (or similar hook and loop fastener) type fastener which provides for size adjustments.

Figure 3:
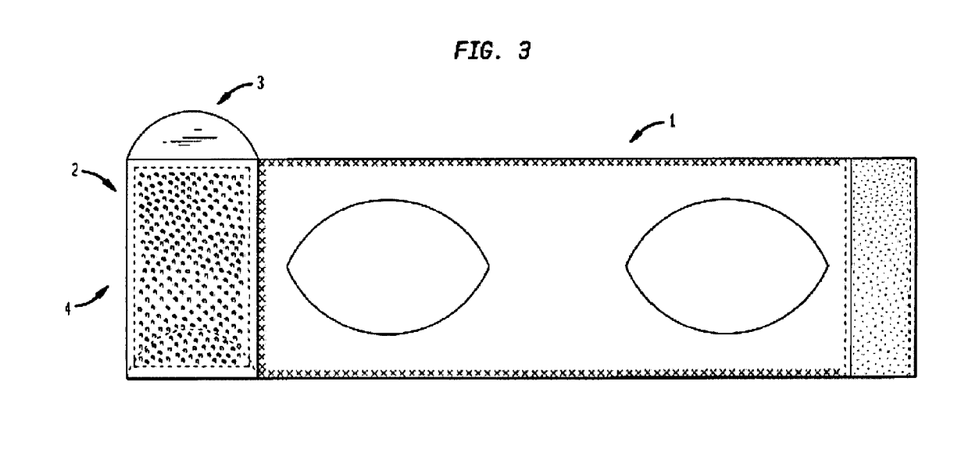
FIG. 3 is a perspective view of the fenestrated band of the invention before it is applied to the patient.
Figure 4:
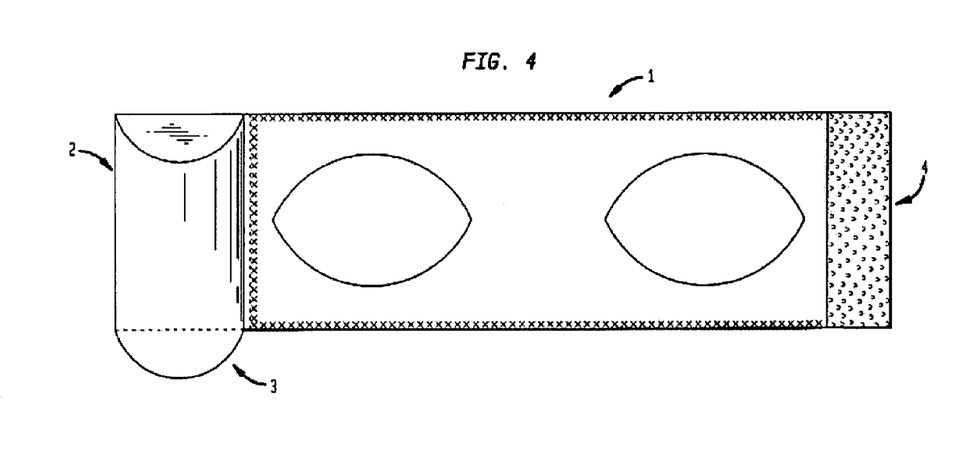
FIG. 4 is a perspective view of the fenestrated band as it would be applied to the patient and the body engaging surface

The drawings depict the flat surface of the semi-cylindrical bolster as having a patch of material 4, shown in FIGS. 1 and 3 consisting of multiple laterally spaced short strips of textile pile material wherein a plurality of hook strips 4, FIGS. 2 & 4 at the distal end and opposing side of the band is suitably attached to the outer pile material on the bolster when encircled around the body and fastened in the front.

As preferred, the strips of pile material are secured by secure and suitable stitching to the flat surface of the bolster which will receive the hook strips. Hook strips may be of a type such as is disclosed by de Mestral in U.S. Pat. No. 2,717,437 ("de Mestral"), wherein the hook strip is constructed with tiny fiber hook elements extending outwardly from one side of a backing material which will become embedded and adhere to the soft pile material when pressed together.

Because the fastening means is described by de Mestral, a further description thereof is deemed unnecessary. In fact, it is to be understood that other fastening devices may be employed without departing from the invention. This also applies to the semi-cylindrical bolster which can be replaced by any other shape which accomplishes the means of support as a bolster and breast separator. This can be especially useful since implants must be centered and maintained over the nipples, even if the natural breast are divergent. Also, at times when the surgeon "overcreates" the breast pocket for implant placement, the doctors over cut and the tissue over the sternum is separated and an internal stitch is necessary to adhere and maintain the tissue in place so that the implant does not shift. The band's night use will encourage healing and tissue repair in proper alignment and perhaps avoid the occurrence of shifting.

The semi-cylindrical bolster, or pillow, of the comfort band can be of a soft but firm absorbable sponge-like material that, perhaps, has perspiration absorbing qualities that modern diapers have which pull the perspiration from the first layer, thereby protecting the skin, into the more absorbent core material. Using a similar material with a bacteriostatic function can decrease infection incidences when used in the geriatric population. Healthcare professionals, caretakers, and other users should be attentive that the pillow does not become so saturated that its main objective has been defeated. This is one incidence where using the separate, or interchangeable pillow component is best and easiest to use. When used in the medical field, the use of a non-latex material should be considered for those patients with known Latex allergies.

Referring now to FIG. 1, a stretchable and adaptable body conforming knit material of approximately 74 cm long by 50 cm wide of a material is laid out to its fullest dimensions which when folded in half lengthwise will yield a lower panel A and an upper panel B. With this orientation in mind, reopen it to its fullest dimensions.

In order to construct a preferred embodiment of the present invention, sew a permanent and secure patch of nap pile material approximately 8 cm long by 5 cm wide with its length to the right edge 4 of panel A. Next, maintaining original orientation, sew a 8 cm by 5 cm patch of hook strips to the left edge 4 of panel B. Fastening means have now been secured so that when the band is constructed and is encircled about the chest it will be in overlapping relationship to the pile material over the flat surface of panel A. Next flip panel A so that panel A now faces panel B and is inside out. Leaving a 5 mm free edge on top sew a permanent seam to the right edge of panels A and B together which will create a right angle pocket. Flip to the original orientation. By means of a scissor obtain a sponge-like material, cut and shape the semi-cylindrical bolster to the following dimension, flat wall surface 6.5 cm wide, height 9 cm, cylindrical depth dimension of 12.2 cm round from its flat wall surface so that it yields a total circumference of up to 18.7 cm. At its top and bottom base surfaces the above dimensions should yield a 4.8 cm wide flat surface from its 6.5 cm wall. Next, enclose and position the semi-cylindrical bolster to the extreme right between panel A and B with its flat surface facing panel A while the semi-cylindrical bolster faces panel B. Invert 5 mm of bottom edges of panels A and B and sew the length of the band leaving a 5 mm free edge to the left of the band. Sew a permanent and secure seam to the left of the semi-cylindrical bolster, securing it to its compartment.

Invert the free 5 mm left edges of panels A and B and sew permanent seams. The band is now fully constructed and ready to apply by placing the cylindrical surface of panel B over the sternum, between the breast and encircling the band around the back and chest so that the free end of the band with the hook strips may be fastened over the nap pile material of panel A.

Referring now to FIG. 2, a stretchable and adaptable body conforming knit material of approximately 60 cm long by 20 cm wide of a material is laid out to its fullest dimensions which when folded in half lengthwise will yield a lower panel A, and a panel B. With this orientation in mind, reopen it to its fullest dimensions.

Sew a permanent and secure patch of nap pile material of approximately up to 8 cm long by 5 cm wide with its length to the right edge of panel A, next maintaining original orientation sew a 8 cm by 5 cm patch of hook strips to the left edge of panel B. Fastening means have now been secured so that when the band is constructed and is encircled about the chest it will be in overlapping relationship to the pile materials over the flat surface of panel A. Next flip panel A so that panel A now faces panel B and is inside out. Leaving a 5 mm free edge on top sew a permanent seam to the right edge of panels A and B together which will create a right angle pocket. By means of a scissor obtain a sponge-like material, cut and shape the semi-cylindrical bolster to the following dimension, flat wall surface 6.5 cm wide, height 9 cm, cylindrical depth dimension of 12.2 cm round from its flat wall surface so that it yields a total circumference of 18.7 cm. At its top and bottom base surfaces the above dimensions should yield a 4.8 cm wide flat surface from its 6.5 cm wall. Next, enclose and position the semi-cylindrical bolster to the extreme right between panel A and B with its flat surface facing panel A while the semi-cylindrical bolster faces panel B. Invert 5 mm of bottom edges of panel A and B and sew the length of the band leaving a 5 mm free edge to the left of the band. Sew a permanent and secure seam to the left border of the semi-cylindrical bolster, securing it to its compartment. Measure approximately 2 cm from this last seam, mark it. Next measure out and mark an ellipsis measuring 11 cm long by 7 cm tall from 1.5 cm from the top and bottom edges so that its mid axis and highest point is at 90 degrees. Evenly cut fenestrations, invert its double edges approximately 2 mm's and seam edges of fenestration closed. From the left edge side of this fenestrations measure 24.5 cm on the band next measure out and cut the same dimensions of the first fenestration. Seam fenestrations edges closed together as before. Fenestrations are complete. Invert the free 5 mm left edges of panels A and B and sew together with permanent seams. The band is now fully constructed and ready to apply by placing the cylindrical surface of panel B over the sternum, between the breast and encircling the band around the back and chest so that the free end of the band with the hook strips may be fastened over the nap pile material of panel A.

Figure 5:
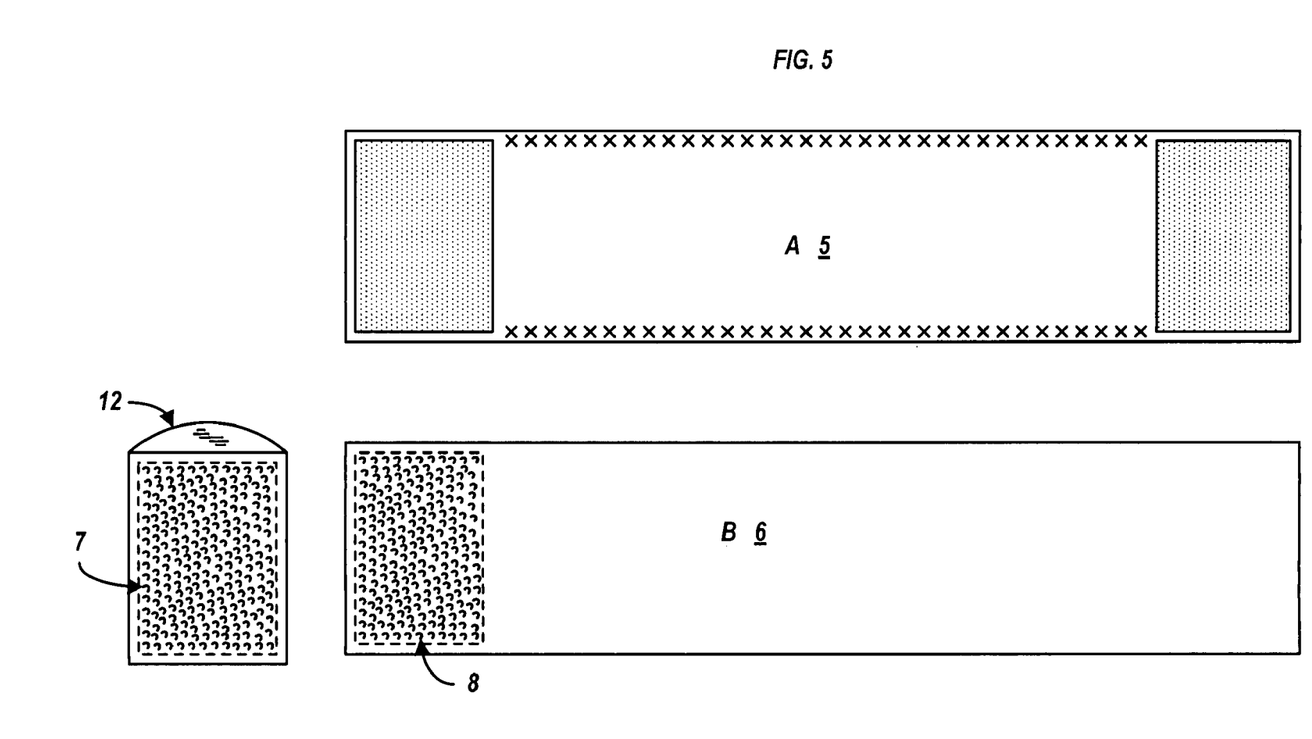
FIG. 5 is a perspective view of the double nap version of the solid band before it is applied to the patient.

While the pillow can be attached as a single component within the band, in an alternative embodiment of the invention, the pillow is a separate component of the band with interchangeable pillow sizes for use at different times depending on the changing conditions and needs of the breasts. When the pillow is a separate component it is attached to one of the band ends with VELCRO™ (or similar hook and loop fastener), the same way it is secured around the torso. This version is depicted in FIG. 5, and is referred to as the double nap version. The double nap version is constructed in a similar manner as the preferred embodiment, but the pillow 12 is not sewn directly into the panels A and B. Two patches of nap are attached to the left and right sides of lower panel A 5. The hooked surface 7 of pillow 12 is attached to the nap on the left side of panel A. Panel B 6 has a single hooked surface 8 attached to its left side. Panel B is folded and sewn to the reverse side of panel A and the hooked surface 8 is attached to the nap surface of the right side of panel A after wrapping the band around the torso. This design of the breast comfort band may be varied by creating a stretchable solid or fenestrated band with the nap material on both ends and hook loop opposite one of the ends to receive the nap surfaces of the pillow.

This comfort band's non-bulky design is free of clips and pins so that it may, in addition to night use, also be used under a traditional bra or sports bra to prevent skin chaffing and absorb perspiration while the agile user exercises, is in extreme high temperatures or is active in the upright standing position and at any time of the day. The pillow between the breasts then serves as a perspiration absorber/barrier that can be changed to a dry pillow when the interchangeable pillow version is used.

Figure 6A:
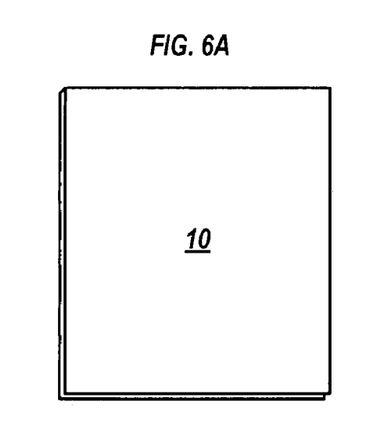
FIG. 6A depicts a nap curtain in the closed position.
Figure 6B:
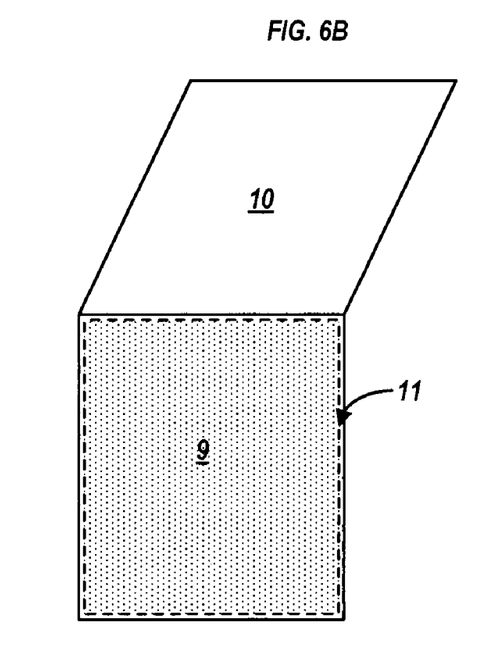
FIG. 6B depicts the nap curtain in the open position, wherein the nap pile is exposed to receive the hook portion on the flat surface of a pillow.

The comfort band's objective of absorbing perspiration with the use of a sports bra can be incorporated by either redesigning a sports bra with the pillow component attached to its body or by making available the pillow component independently. This will require a patch of nap material with a "nap curtain" that can be sewn onto the sports bra. The nap curtain is depicted in FIGS. 6A and 6B and consists of a nap surface 9 that can receive the hooked surface 7 of a pillow 12, a curtain swatch 10, and a seam 11 connecting the nap surface 9 and curtain swatch 10. The nap patch 9 will receive the pillow part 7 when the user chooses. If the user chooses not to use the pillow, she may still utilize the sports bra by securing the curtain 10 over the nap 9 in order to prevent skin irritation.

Figure 7:
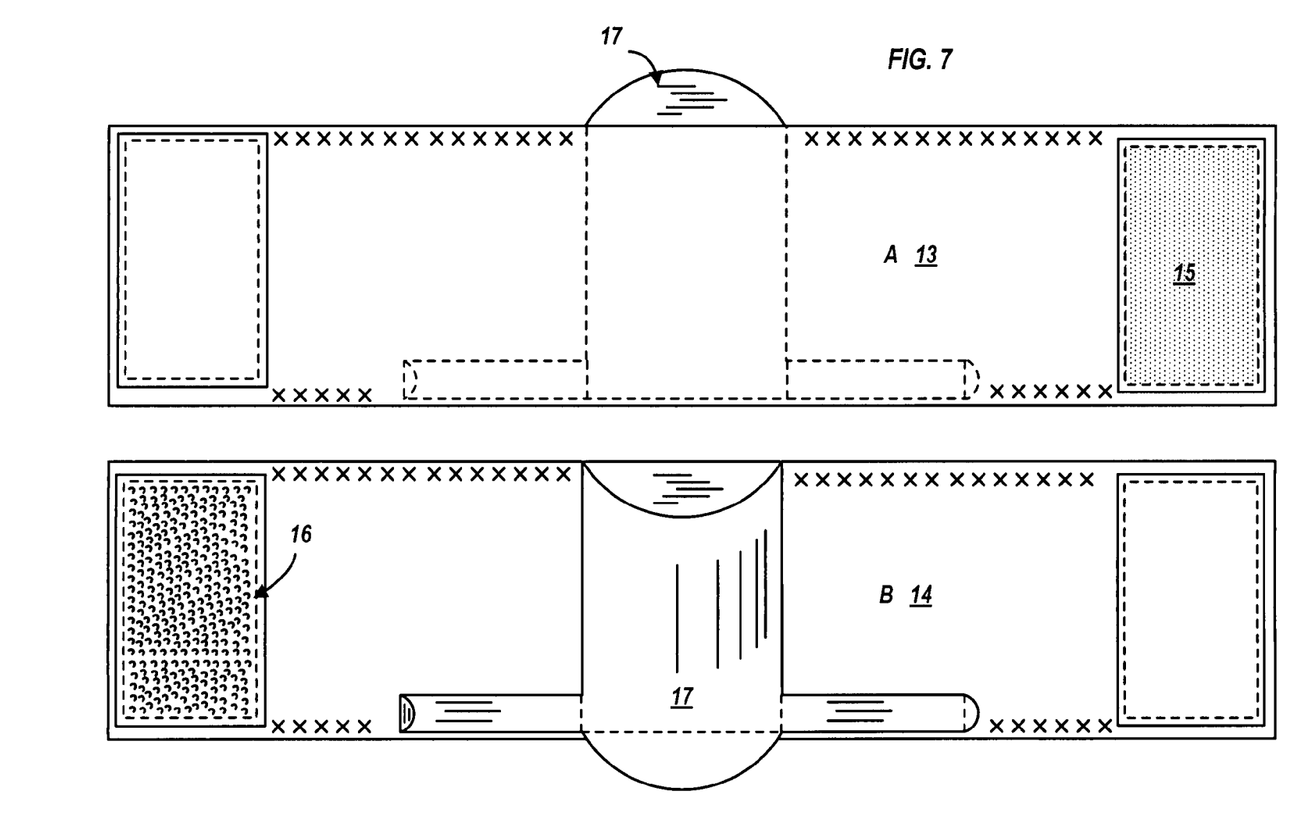
FIG. 7 shows a version of the breast saver comfort band with a central pillow with right and left extensions/inframammary pillow centrally placed on the band which closes at the back.

The concept of having a pillow between the breasts may also be an advantage when this pillow component is extended to underneath the breast. This alternative embodiment is depicted in FIG. 7. Shown is a panel A 13 with a patch of nap 15 attached to the right side of panel A 13 and a centrally placed pillow with extended inframammary portions 17. Panel A 13 is folded and sewn to the reverse side of panel B 14 wherein panel B 14 consists of a hooked patch 16 on the left side and a centrally placed pillow with extended inframammary portions 17. The pillow 17 will serve the same advantages as the medial breast pillow 12, i.e. absorption and breast stabilization. This particular design is most beneficial for breast augmentations or reductions with inframammary incisions. Incisions on breast reductions usually run from the inferior areola to inframammary area. Having the inframammary pillow will protect the incision, absorb drainage and reduce breast movement that may cause pain.

Figure 8:
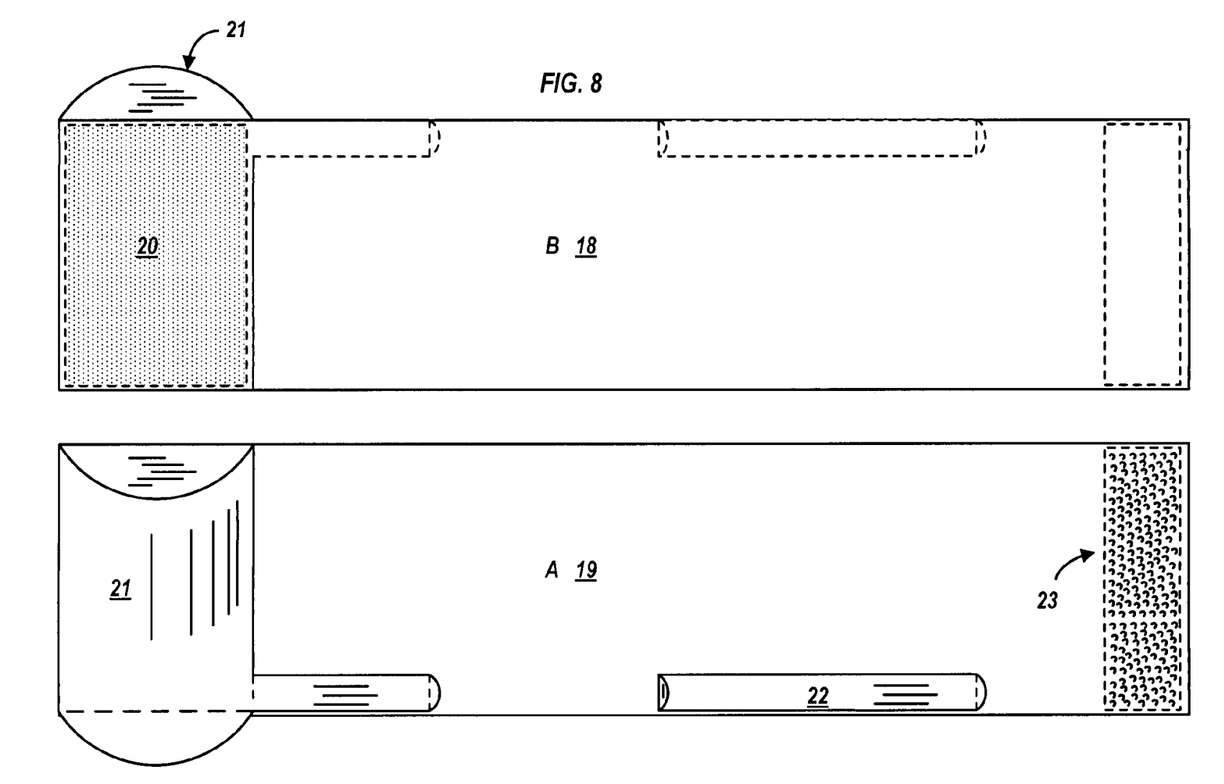
FIG. 8 shows a version of the breast saver comfort band with one inframammary pillow attached to the central pillow and one separate inframammary pillow that may be placed according to breast spacing need.

FIG. 8 shows an interchangeable embodiment of the band with a right inframammary pillow. The pillow 21, with its extension, is placed at the left end of panel A 19, a hooked patch 23 on the right end, and a horizontally placed inframammary pillow 22 between the hooked patch 23 and inframammary pillow 21. With a nap patch 20 on the left side of panel B 18 and panel 18 attached to the reverse left side of panel A 19, the band is wrapped around the chest and secured as the original at the front of the chest. This version allows proper inframammary pillow placement by placing a VELCRO™ (or similar hook and loop fastener) patch on the band and securing the VELCRO™ (or similar hook and loop fastener) backed inframammary pillow on the band at its most beneficial placement, depending on the distance between breasts.

The comfort band design shown in FIG. 6 may also be used for mastopexy, i.e. a procedure to correct for Mammary ptosis (drooping). The operation involves excision of redundant breast skin to reconstruct breast contour and symmetry.

With postpartum patients in conjunction with breast pads that absorb colostrum and milk. The band will keep the pads secure since the pillow will prevent breast shifting throughout the time the band in used. Breast pads usually shift inside the brassier cup in relation to the user's activity and proper cup fitting. When the comfort band, in any variation described, is used with a traditional bra the user will achieve optimal breast stabilization. The use of these together will minimize the movement of the engorged breast, and as a result will decrease pain and discomfort.

After a breast augmentation operation, bandages, e.g. ACE™ bandages, are typically employed to stabilize the implants and dressings. Aside from the nature of the surgery, the bandage is wrapped so firmly and occasionally too tight around the upper torso or chest that it causes further difficulties in breathing associated with inhalation and chest expansion.

When the bandage is applied the patient is generally still under anesthesia and requires that the surgical team hold the patient up to allow the wrapping of the bandage around the torso. This requires a minimum of two people and if the patient is still intubated or has an oral airway an anesthesiologist must protect the accidental dislodging of the airway tube due to gross movement of the patient. This is also time-consuming because while holding up the patient any blood or fluids that have drained toward the patient's back must be cleaned off the skin before applying the dressing. Use of the comfort band will eliminate the use of a multi-layered bandage and can easily be applied by using immobilized patient nursing techniques with less personnel. It will also stabilize the implants while the patient is in the side-lying position at night. Sleep is improved as well.

The disclosed comfort band allows for easier post-operative exams since its application and removal is now preferably of a single layer. This single layer also facilitates self-dressing changes since the patient will not have to wrap a bandage multiple times.

A fenestrated comfort band accomplishes the same result as the solid band as well as facilitates night breast feeding. Having these fenestrations also allows for air exposure for users who have areola irritations. These irritations can result from breast feeding or areola reconstruction or any other discomfort in close proximity to the areola. The fenestrations and the band incorporating it are made of such stretchable material with memory that allows various breast sizes to be accommodated while maintaining the integrity of the garment for multiple uses and laundering.

The comfort band's basic design may also be used as a compression bandage. Compression on wounds and incisions is necessary to reduce blood loss and swelling. The band may be wrapped around the body of the area to be treated with respective tightness while the space occupying component, i.e. the pillow part, may be placed over the wound to reduce the blood loss or swelling. It will also reduce the amount of sterile or clean dressing needed when dressing a wound, as well as being quicker and easier while achieving the same compression derived from "fluffing" regular dressing sponges. This fluffing of sponges (opening sponge gauze to create bulk and occupy space) usually requires either tape or multilayering of an ACE™ bandage to secure the gauze. Use of the comfort band will eliminate such use as well as reduce skin adhesive irritation.

Figure 9:
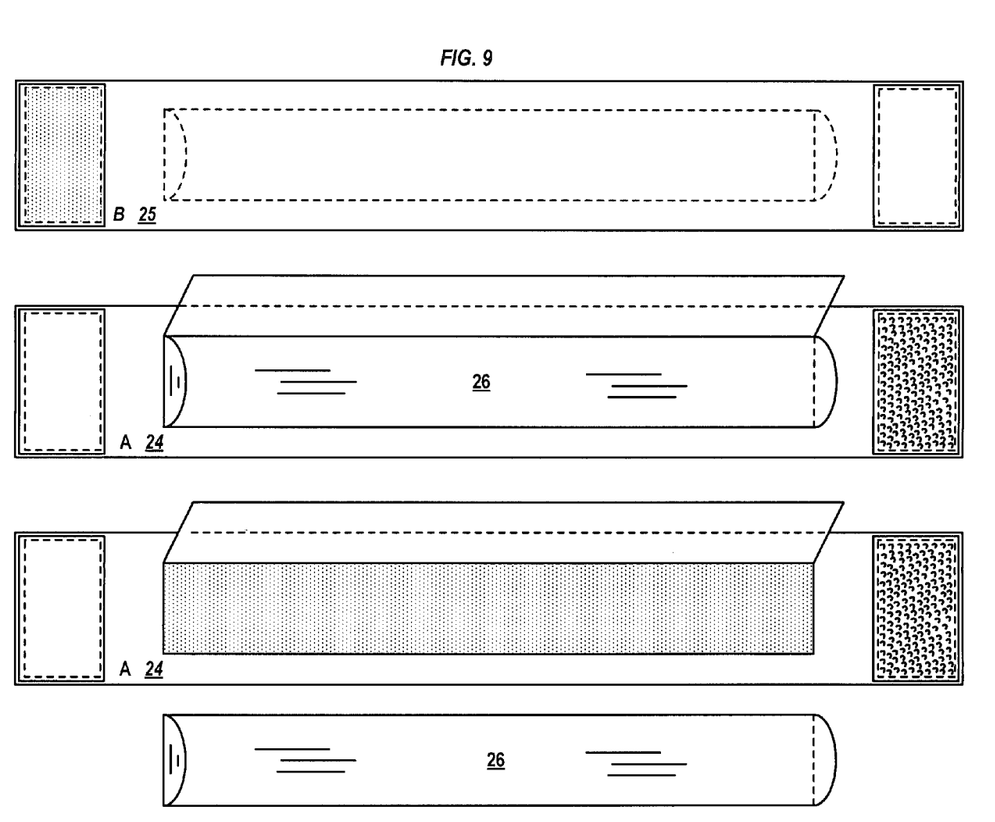
FIG. 9 depicts a pillow placed horizontally on the band (Double Nap version).

Common anatomical areas where compression is needed are the limbs, chest, head, and neck. In the limbs it may be used when a space occupying mass is removed and deep compression is necessary. Using the double nap with curtain version depicted in FIG. 5, the present invention may, with a change in its design from vertical to horizontal pillow placement on the band, also be used for head and neck, as well as for facelifts. A depiction of this embodiment is illustrated in FIG. 9. This embodiment of the invention has a minimum of one nap to receive pillows according to incision length. A horizontally placed pillow 26 is centered on the naps of panel A 24 with a hooked patch on the right side of panel A 24. Panel B 25 is folded and adhered to the reverse side of panel A 24, with a patch of nap on the left end of panel A. The band is secured in an overlapping fashion with its hooked patch on the right side of panel A 24 to the nap on the left of panel B 25. Again, this embodiment will reduce the use of tape and ACE™ bandages, time and supplies regularly used in such dressings while achieving the same results.

As a compression bandage it may also be used for open heart incision dressing as an alternate to tape that sometimes does not adhere due to body hair. Long spinal incisions may also benefit from the use of the band.

When space occupying masses are removed or when deemed necessary for other reasons, drains are placed in the wounds. Drain placement requires securing its receptacle often with a safety pin or tape directly on the dressing. The use of the band will still accommodate this need.

Figure 10:
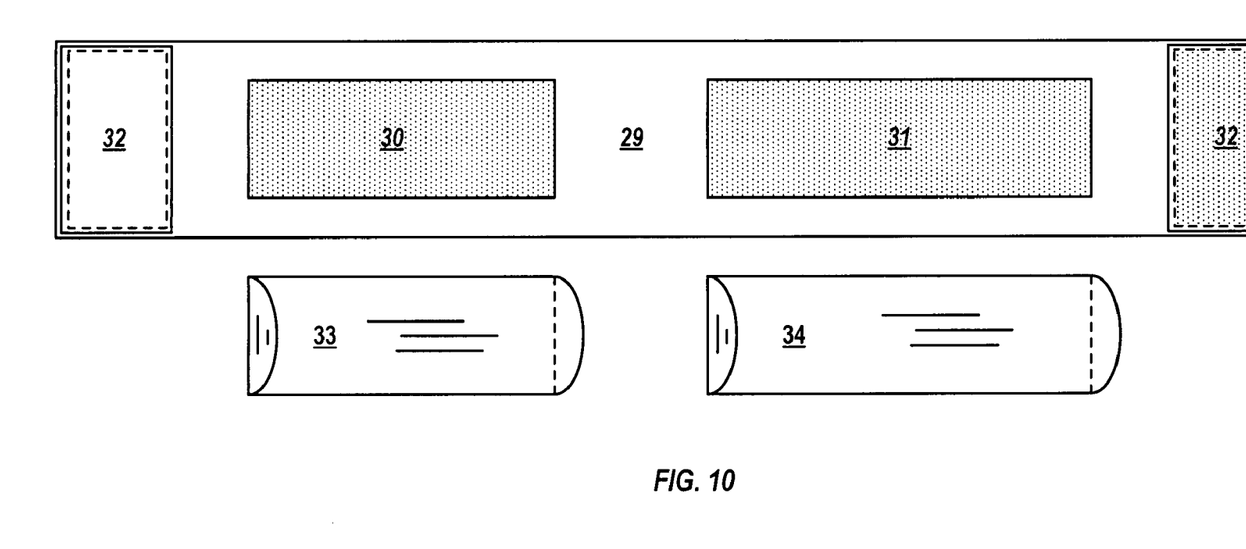
FIG. 10 shows two horizontally placed removable pillows on the band.

The change to the vertical placement position of the pillow can also be accommodated to allow for multiple placement of pillows allowing for a longer compression area. This is achieved with placement of numerous pillows, or one long pillow, along the length of the band and secured on with the same VELCRO™ (or similar hook and loop fastener) features. As shown in FIG. 10, a band 29 has VELCRO™ (or similar hook and loop fastener) attachments 32 at both ends with nap patches 30 and 31 placed in between. Pillows 33 and 34 have hooked patches for placement onto nap patches 30 and 31, respectively. While only two pillows are shown in FIG. 10, any number may be used depending on the need and use for different situations. This may be used for facelifts where the incisions run along the hairline and in front or behind the ear. Depending on the need for compression, respective pillows may be removed and its nap covered with the attached nap curtain.

Figure 11:
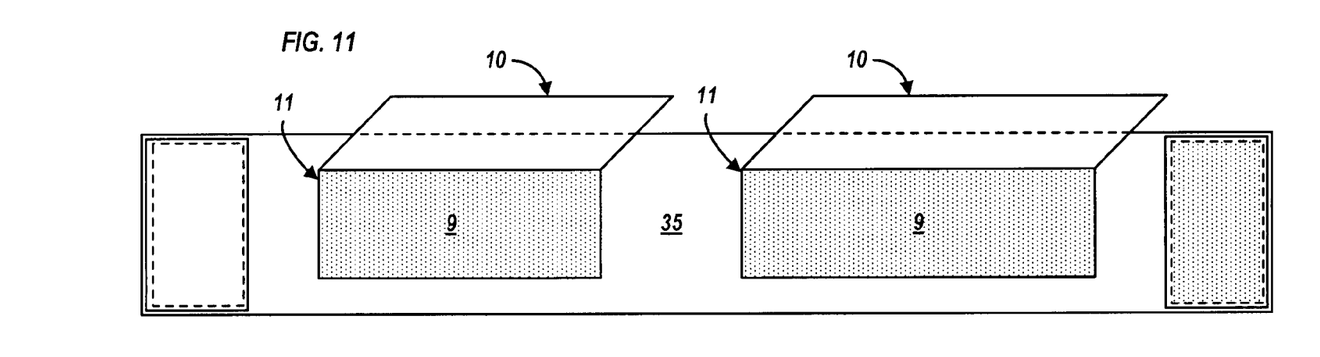
FIG. 11 depicts the nap curtain of FIG. 6 incorporated for use with the band, including two nap curtains secured to the band in the open position.
Figure 11A:
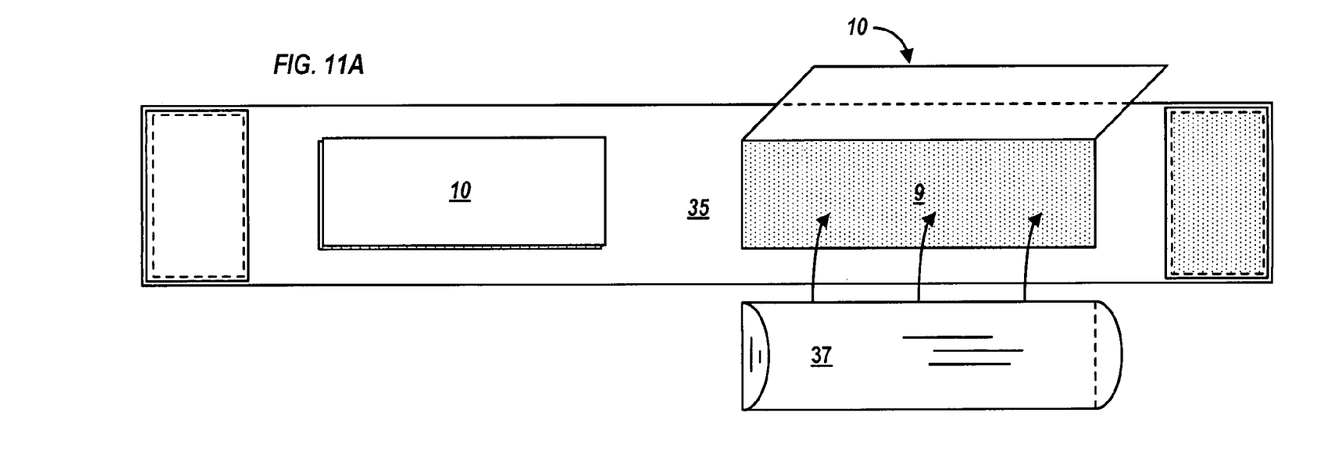
FIG. 11A shows one of the nap curtains of FIG. 11 in the closed position, while the second nap curtain remains open to allow the attachment of a pillow to the nap.

Referring to FIG. 11, two nap curtains are attached to band 35. The nap curtain comprises a nap patch 9, which is attached to the band 35, a nap curtain 10, and a seam 11 to connect them. As shown in FIG. 11A, a pillow 37 with hooks on the back can be attached to the nap patch, while the second nap 9 is covered by the curtain 10 when no pillow is attached. The nap curtain will prevent skin irritation once its respective pillow is removed.

Figure 12:
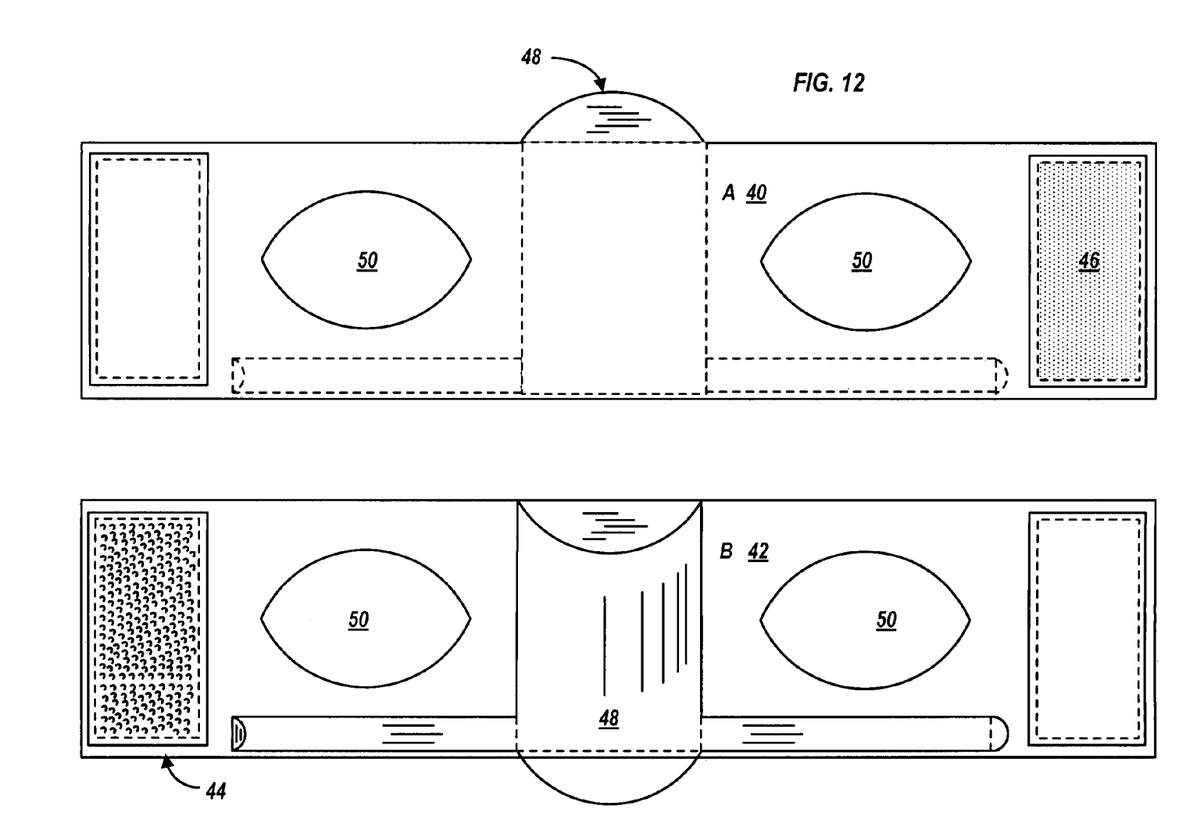
FIG. 12 shows fenestrated central and inframammary pillows.

With regards to FIG. 12, shown is a panel A 40 with a patch of nap 46 attached to the right side of panel A 40 and a centrally placed pillow with extended inframammary portions 48. Panel A 40 is folded and sewn to the reverse side of panel B 42 wherein panel B 42 consists of a hooked patch 44 on the left side and a centrally placed pillow with extended inframammary portions 48. The pillow 48 will serve the same advantages as the medial breast pillow 12, i.e. absorption and breast stabilization. This particular design is most beneficial for breast augmentations or reductions with inframammary incisions. Incisions on breast reductions usually run from the inferior areola to inframammary area. Having the inframammary pillow will protect the incision, absorb drainage and reduce breast movement that may cause pain. Also, fenestrations 50 are added by the method described above. The fenestrations 50 allow for breast exposure to prevent or relieve areolar irritation or to allow for breast feeding.

Figure 13A:
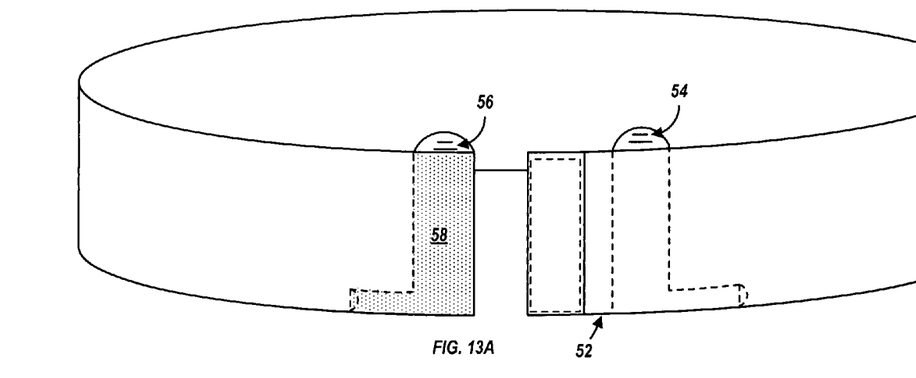
FIG. 13A illustrates the outer portion of a band incorporating an elastic wedge between the fastening means and the inframammary pillow.
Figure 13B:
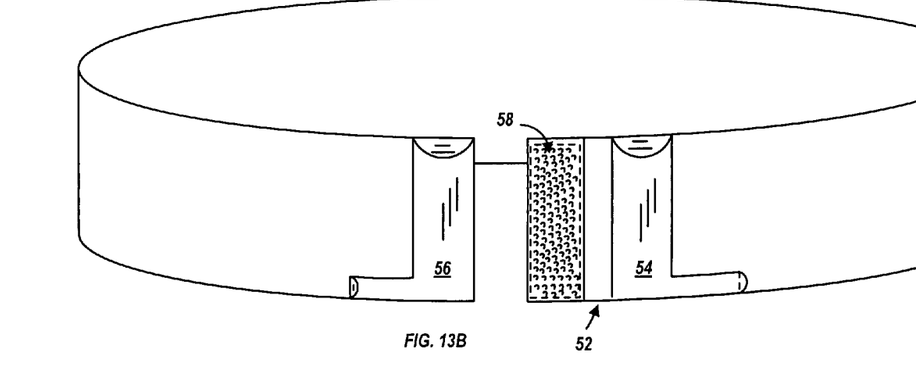
FIG. 13B shows the inner portion of the band shown in FIG. 13A.

Finally, regarding FIGS. 13A and 13B, shown is yet another embodiment of the present invention. FIG. 13A depicts the outer portion of the band, while FIG. 13B shows the inner side of the band. In particular, an elastic wedge 52 is inserted between the pillow 54 and the VELCRO™ (or similar hook and loop fastener) 58. The elastic wedge 52 at the end of the band provides for extra tightness around the chest. As depicted in FIG. 13A and 13B, the bolster is divided into right 54 and left 56 semi cylindrical L-shapes. This specific shape of bolster will accommodate both the right and left breast medially, as well as provide inframammary support. The elastic wedge 52 allows for providing extra tightness, if needed. Use of the band with elastic wedge 52 is best for immediately after breast augmentation and for mastitis.

While the present invention has primarily been described for use in the chest area, the comfort band may also be used on other parts of the body. In particular, the comfort band may be used for sub-mandibular lipectomy or chin liposuction for compression and to absorb tumescent leakage (the combination of IV solution and Lidocaine that is infiltrated into the skin in order to separate tissue layers and then suctioned with liposuction canals) which in turn reduces swelling and shapes the newly contoured area.

The available chin straps now used are double strapped and are wrapped around the chin along the front of the ear and secured on top of the head with the second attached strapped wrapped around the head, resulting in bulky dressing and the possibility of over compression by providing compression to an area of the head that is not necessary and may create a headache. It also still requires the placement of regular gauze at the incision site which makes it appear sloppy.

Facelift (rhytidectomy) incisions are either in front or behind the ear and extend along the top of the hairline to under the earlobe and then curve to the length of the middle of the neck. In using the comfort band with proper placement of the pillows on the band will provide absorbency as well as provide compression needed to reduce the swelling of tissue around the incision. At present, if a chin strap or a face strap is used it will still require the use of regular gauze over the incision which creates a bulkier and less aesthetically pleasing appearance. This gauze also tends to shift causing shearing of the actual incision.

In other facial surgeries such as mastoidectomy, which require an incision in front or behind the ear, the comfort band may be placed along the band so that it stays away from the ear and against the skull. The comfort band will replace fluff dressing sponges and it will, as required for mastoidectomies, stay high around the head so that it does not fall over the eyes and stay over the hairline and not across the forehead. The comfort band may also be used for a paroidectomy. In essence, the present invention may be used when an absorbent component with a wrap is necessary.

For extremity surgeries such as brachioplasty (aesthetic surgical procedure for the treatment of redundant loose skin and subcutaneous tissue of the upper arm) as well as for use in wrist injuries as commonly seen in suicide slashing, the comfort band will prove useful as a quick compression application band. The comfort band is also useful for leg injuries with bleeding. In addition, poplitieal cysts or other incisions in the back of the knees may also benefits from the advantages of the comfort band's compression as well as aid in the prevention of hematoma. The comfort band provides increased comfort and ease of use over the traditional fluff dressings and ACE™ bandages.

While the present invention has been described with reference to one or more preferred embodiments, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A band for comfort and breast stabilization while the user lays in the right or left lateral position comprising:
   a stretchable and adaptable body strip disposed to encircle the body; and
   first and second sections of the length of said body strip;
   wherein said first section further comprises a semi-cylindrical component of a sponge-like material at one end and a nap material patch on an outer surface of said first section with a cylindrical side adapted to be placed over the sternum, between the breast; and
   wherein said second section comprises a means for connecting an end of said body strip to said nap material patch to form a loop adapted to encircle a user's body; and
   wherein said first and second sections are at least the same height of said semi-cylindrical component.

* * * * *